United States Patent [19]
Bernard et al.

[11] 4,272,448
[45] Jun. 9, 1981

[54] PROCESS FOR THE MANUFACTURE OF ALUMINUM MONOETHYL PHOSPHITE

[75] Inventors: André Bernard; André Disdier, both of Villeurbanne; Michel Royer, Lyons, all of France

[73] Assignee: Philagro, Lyons, France

[21] Appl. No.: 51,753

[22] Filed: Jun. 25, 1979

Related U.S. Application Data

[63] Continuation-in-part of Ser. No. 22,510, Mar. 21, 1979, abandoned.

[30] Foreign Application Priority Data

Mar. 24, 1978 [FR] France ............................. 78 09965

[51] Int. Cl.³ .............................................. C07F 5/06
[52] U.S. Cl. .............................................. 260/448 R
[58] Field of Search .................... 260/448 R; 424/222

[56] References Cited

U.S. PATENT DOCUMENTS

| | | | |
|---|---|---|---|
| 4,139,616 | 2/1979 | Ducret et al. | 424/222 |
| 4,143,059 | 3/1979 | Abblard et al. | 260/448 R |

*Primary Examiner*—Helen M. S. Sneed
*Attorney, Agent, or Firm*—Browdy and Neimark

[57] ABSTRACT

Aluminum monoethyl-phosphite, useful for the protection of plants against fungal diseases, is manufactured in a continuous manner by first preparing a mixture of phosphite compounds, containing at least 70 mol % of diethyl phosphite, then saponifying and neutralizing such mixture with an inorganic base, at a temperature of 20°–85° C., at a pH of 4.0–8.5, and finally reacting the residual aqueous solution of alkaline metal monoethyl-phosphite, continuously withdrawn from the preceding operation, with an approximately stoichiometric amount of a water-soluble aluminum salt at 70°–95° C. and a pH of 3.0–4.5.

21 Claims, No Drawings

PROCESS FOR THE MANUFACTURE OF ALUMINUM MONOETHYL PHOSPHITE

This is a Continuation-in-Part of copending application Ser. No. 22,510 filed Mar. 21, 1979, now abandoned.

The present invention relates to a process for the manufacture of aluminium monoethyl-phosphite.

This compound has been described in U.S. Pat. No. 4,139,616 as belonging to a family of compounds which are valuable by virtue of their good fungicidal properties for the protection of plants against fungal diseases.

In particular, U.S. Pat. No. 4,139,616 describes that this particular compound can be obtained in 3 separate stages, namely initial saponification of diethyl phosphite, in aqueous-alcoholic solution, with potassium hydroxide, then separation of the potassium monoethyl-phosphite by distillation of the alcohol and the water under reduced pressure, and finally reaction, in aqueous solution, of the potassium derivative with hydrated aluminium nitrate. The resulting aluminium derivative precipitates.

This process exhibits the disadvantage that the three stages are carried out discontinuously. Furthermore, the yields are good, but the amounts are low (of the order of a few gramms) because these are laboratory experiments. Finally, from the industrial point of view, diethyl phosphite is a relatively expensive compound because several steps are required for its separation and its purification. Now, since the filing of the two above-mentioned applications, one of the compounds in the family, namely aluminium monoethyl-phosphite, has shown a remarkable combination of physical, chemical and biological properties enabling it to be used and marketed on a large scale as a fungicide for the protection of plants. Under these conditions, the above process is no longer suitable from both the technical and the economic points of view. It was therefore necessary to find a process which can be carried out on large amounts and uses more economical starting materials.

The invention therefore relates to a process for the continuous manufacture of aluminium monoethyl-phosphite, which consists in successively:

(a) preparing a mixture of phosphite compounds, containing at least 70 mol % of diethyl phosphite, (b) saponifying and neutralising this mixture with an inorganic base, at a temperature of 20° to 85° C., whilst keeping the pH at 4.0 to 8.5, it being possible for the ethanol produced by the reaction to be removed continuously by distillation in the form of an aqueous-alcoholic mixture, and then (c) reacting the residual aqueous solution of alkali metal monoethyl-phosphite, which is continuously withdrawn from the preceding operation, with an approximately stoichiometric amount of a water-soluble aluminium salt in accordance with a double decomposition reaction, at a temperature of 70° to 95° C. and at a pH of about 3.0 to 4.5, and continuously withdrawing the precipitate of aluminium monoethyl-phosphite.

The term "phosphite compounds" is understood as meaning, in addition to the diethyl phosphite already mentioned, monoethyl phosphite and phosphorous acid. The respective proportions of these compounds in this mixture are essentially a function of the maximum desired content of phosphorous acid. In fact, this content conditions the formation of aluminium phosphite which is an undesirable impurity because it detracts from the yield and has a low biological activity compared with the corresponding monoethyl phosphite. It is for this reason that, in general, mixtures which are as poor as possible in phosphorous acid will be used. In practice, mixtures containing at most 2 mol % of this acid, and more particularly those containing at least 70 mol % of diethyl phosphite, from 1 to 25 mol % of monoethyl phosphite and from 0 to 2 mol % of phosphorous acid, are preferred.

The mixture of phosphite compounds is a more economical starting material than diethyl phosphite by itself because it is obtained upstream in the manufacture of the latter compound. In fact, this mixture can be obtained in two ways:

either by reaction, assisted by heating, of a mixture of diethyl phosphite and phosphorous acid in accordance with the equation

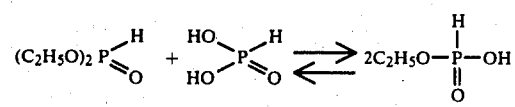

In this case, in order to obtain the desired ternary mixture, it is necessary to start from a binary mixture containing at least 85 mol % of diethyl phosphite and at most 15% of phosphorous acid.

or, advantageously, by reaction of phosphorus trichloride with ethyl alcohol and optionally, but usually, water, depending on the purity of the alcohol employed. This reaction is complex and can be explained by the following theoretical equations:

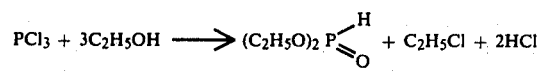

and, in the case of a mixture of alcohol and water, by

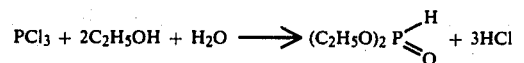

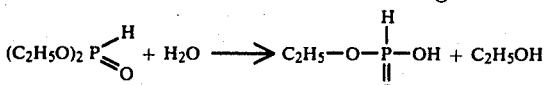

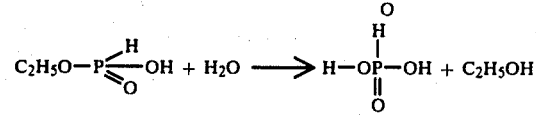

with, as secondary reactions caused by the formation of hydrochloric acid,

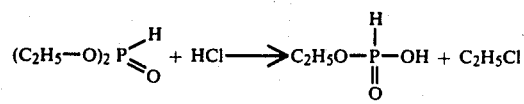

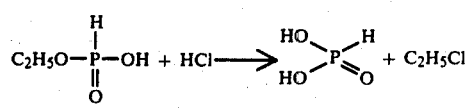

In practice, the reaction is carried out at a temperature of 30° to 80° C. for a duration of a few minutes to one hour.

These equations clearly show that hydrochloric acid considerably changes the mixture of the phosphite compounds; in itself, however, this mixture is very stable. Logically, it is then proposed to remove the gas, but complete removal requires a special operation which does not form an integral part of a continuous process because of the large volume of gas which is to be cleared rapidly. The value of the invention is in fact that it provides a continuous process, although at least one of the stages is not suitable for this process.

The hydrochloric acid and the ethyl chloride produced can therefore be at least partially removed by degassing (especially stripping) and/or neutralisation. If the hydrochloric acid is removed at this moment, the following operation requires less base. In practice, it is advantageous, in order to ensure a continuous process, if the removal is only partial and can then be carried out normally under the reaction conditions (temperature). Thus, at the second step of the process, the medium still contains hydrochloric acid.

The use of water in the process exhibits several advantages; firstly, there is a saving on the starting materials (a less purified alcohol is employed), secondly, water restricts the production of ethyl chloride in favour of hydrochloric acid which can be removed more easily, and finally, water assists the formation of monoethyl phosphite. However, an excess of water would give rise to an excess of monoethyl phosphite, beyond the maximum content of the starting mixture, in accordance with the equation:

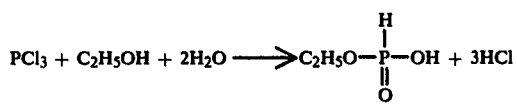

It is for this reason that, in practice, aqueous-alcoholic mixtures contianing at most 15%, and preferably about 10%, by weight of water are used.

The second step of the process according to the invention consists in continuously saponifying and neutralising the mixture of phosphites, which may contain hydrochloric acid, in the form in which it leaves the preceding stage, with an inorganic base, i.e. essentially a strong base, preferably in aqueous solution, e.g. an alkali metal hydroxide, such as sodium hydroxides or potassium hydroxide, or also ammonia, or alkaline earth hydroxides such as calcium or magnesium hydroxide. The cations of these strong inorganic bases are hereinafter represented by Me.

This reaction takes place in accordance with the following equations:

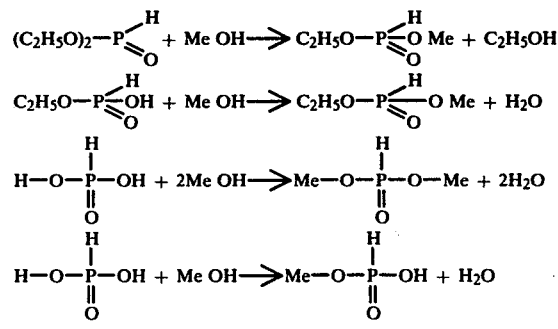

The amount of the basic solution is adjusted in accordance with the stoichiometry of the reaction described above, in order to ensure the saponification of the diethyl phosphite and also the neutralisation of the monoethyl phosphite, the phosphorous acid and the hydrochloric acid. In practice, solutions having concentrations varying between 20 and 50% are used.

This reaction is exothermic and it is necessary, in practice, to keep the reactor at a temperature between 20° and 85° C. and to stir the mixture in order to avoid any local excessive concentration of the base.

The pH must be kept at least between 4.0 and 8.5 in order to ensure the formation of the Me monoethyl-phosphite. The reaction can preferably be carried out in a single reactor at a temperature of 65° to 85° C. and at a pH between about 7 and 8. However, two reactors can be employed. In the first, which is kept at a moderate temperature (about 30° C.), the flow rate of the base is adjusted so that the pH of the medium is equal to at most 4.0. The residence time is 3 to 6 hours, depending on the adjustment of the amounts (and hence of the flow rates). The medium, which is already rich in sodium monoethyl-phosphite, is transferred continuously into a second reactor in which the reaction is completed by adding a further amount of inorganic base at a pH kept at a value of at most between 8 and 8.5 and at a higher temperature, of 60° to 85° C.

The saponification reaction liberates ethanol which, under the conditions in the single reactor or in the second of the two reactors, is preferably removed by continuous distillation in the form of an aqueous-alcoholic mixture. The reaction medium is therefore virtually an aqueous solution, at about pH 7, of Me monoethyl-phosphite and Me chloride with a small amount of Me phosphites.

For the whole of this continuous step, the residence time is about 1 to 6 hours in practice.

The aqueous-alcoholic mixture, which is rich in alcohol, is preferably recycled in order to feed the first stage of the process.

The concentrated aqueous solution (of about 20 to 70% strength) of Me monoethyl-phosphite, which may contain Me chloride, is withdrawn continuously, whilst hot, and directed, at a temperature between about 70° and 95° C., towards another reactor in which the third stage of the process, referred to as the double decomposition stage, takes place. This reactor continuously receives, at the same time as the solution of Me monoethyl-phosphite, an approximately stoichiometric amount of an optionally hydrated water-soluble aluminium salt. The latter can be added either as a solid, which avoids adding water to the reactor, or as an aqueous solution. The reaction is kept at a temperature between 70° and 95° C. and at a pH between about 3.0 and 4.5. Under these conditions (with a residence time of at least 30 minutes), aluminium monoethyl-phosphite is formed in accordance with the following equation of a double decomposition reaction, illustrated with aluminium sulphate:

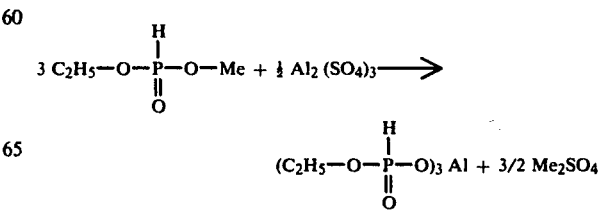

Apart from the sulphate, which is the most common salt, it is possible to use other water-soluble aluminium salts, such as e.g. the nitrate which has a better solubility in water, and this improves the precipitation of the aluminium ethyl-phosphite. An alkali metal aluminate can also be suitable, although it requires the addition of an acid, e.g. hydrochloric acid, but the yields obtained are lower than those obtained with the abovementioned salts.

The formation of aluminium ethyl-phosphite is fairly rapid and the compound readily precipitates because of its low solubility in water. However, this solubility is still not negligible and must be restricted as much as possible in this reaction, because, in solution in an acid medium, the compound decomposes by hydrolysis to give undesirable aluminium phosphite. Moreover, this tendency increases with the temperature of the reaction medium.

In order to overcome this disadvantage, it is necessary to increase the amount of soluble salts in the medium. Because the process is continuous, the aqueous solution may already contain, in addition to the aluminium ethyl-phosphite, a substantial amount of an Me chloride resulting from the preceding stage. In the third stage, another water-soluble salt can be added without any other effect on the reaction, such as e.g. sodium sulphate; however, any other equivalent salt can be used.

Finally, the loss of aluminium ethyl-phosphite by hydrolysis can be restricted by reducing the amount of water empolyed, and this concentrates the aqueous solution. In this respect, the possibility of introducing the water-soluble aluminium salt as a solid is move favourable than the introduction of this same salt in aqueous solution. Furthermore, for the same purpose, the water can be removed during this third step.

The precipitated product is filtered off and then washed hot in order to remove the soluble salts. After drying, a white product is obtained with a good yield (above 85%) and an excellent purity (above 95%).

In order to improve the yield of this reaction, it is also possible to employ a slightly greater amount of one of the reactants, but the excess must not be greater than 20 mol %. This reactant which is in excess is preferably the water-soluble aluminium salt, in which case the reaction can be carried out in a single reactor and a compound is obtained which can be isolated under very economical conditions.

The product obtained by the continuous process according to the invention can exist in the form of a uniform powder (mean particle size between 100 and 350 microns) having a density between about 0.7 and 0.9 and a low moisture content (<20%), especially in the case where the reaction is carried out with an initial excess of aluminium salt. This is particularly remarkable because this form is totally new, the product obtained discontinuously, either in the laboratory or even in a semi-scale process, being a fine powder having a density of 0.4 to 0.6 and a moisture content of the order of 25% and consequently being less convenient to filter, requiring a longer drying time and being more difficult to handle (dusts) and to formulate into a wettable or soluble powder, in fungicidal compositions for spraying.

The following examples are given without implying a limitation in order to illustrate the process according to the invention. Unless otherwise stated, the percentages are expressed by weight.

EXAMPLE 1

A. Phosphorus trichloride (55 g/hour, 4 mols/hour) and 90% strength ethanol (520 g/hour, about 10% excess), i.e. containing 90% of ethanol and 10% of water, are fed by means of dip tubes, continuously and whilst stirring, into a reactor I, referred to as a reactor for the preparation of phosphite mixtures, which is kept at 60° C. by the external circulation of cold water.

The volume of the reactor is such that the residence time is 5 minutes. The gases formed (HCl and ethyl chloride) are partially removed and then sent on to be destroyed (alkaline washing and solvent extraction).

B. The reaction product, which consists of a mixture of phosphites (80 mol % of diethyl phosphite, 18 mol % of monoethyl phosphite and 2 mol % of phosphorous acid) and hydrochloric acid, is sent for saponification and neutralisation into a reactor II, kept at 75° by the circulation of hot water, in which it is treated with a 50% strength aqueous solution of sodium hydroxide at a flow rate (200 g/hour) which is such that the pH of the medium is adjusted to 7.5.

Under these conditions, the residence time is about 1 hour.

A mixture containing sodium ethyl-phosphite, ethanol, water, sodium chloride and a small amount of sodium phosphite is withdrawn from the reactor II. This mixture is then distilled continuously in order to remove the ethanol, produced by the saponification of the diethyl phosphite, in the form of an aqueous-alcoholic solution containing 80% by weight of alcohol. An aqueous solution remains which contains 29% by weight of sodium ethyl-phosphite and 11% of sodium chloride (flow rate: 1,960 g/hour).

Under these conditions, the yield of sodium ethyl-phosphite is 97%, relative to the phosphorus trichloride employed.

C. The aqueous solution of sodium ethyl-phosphite at a temperature of 85° C. is then introduced continuously, whilst stirring, into a reactor III, referred to as a double decomposition reactor, together with a 28% strength aqueous solution of aluminium sulphate at a flow rate of 864 g/hour, i.e. with an excess of 10 mol %, relative to the sodium ethyl-phosphite, at the same temperature. The medium is at a pH of 3.8. The aluminium ethyl-phosphite precipitates, the reaction medium is kept in the precipitation reactor for 1 hour and the slurry is then withdrawn and separated on a filter. The moist product (residual moisture content of 8%) is washed with hot water and then dried at 90° C. The dry product is obtained at a rate of 400 g/hour. The yield of isolated product is 88% relative to the sodium ethyl-phosphite (the remainder of the 100% being in the mother liquors and washing waters which can optionally be recycled) and 85% relative to the phosphorus trichloride employed. The content of aluminium phosphite in the isolated product is less than 2%. The latter is in the form of a powder having a density equal to 0.9 and a particle size distribution which is such that 88% of the particles are smaller than 500 microns and 98.5% are larger than 63 microns.

EXAMPLE 2

The same results are obtained by following the procedure of Example 1, except that stage B is carried out in two reactors. The first (IIa) is kept at 30° C. by the circulation of cold water; the mixture is treated continuously therein with a 30% strength by weight aqueous solution of sodium hydroxide at a flow rate (1,900 g/hour) which is such that the pH is fixed at between 4 and 4.5.

Under these conditions, the residence time is about 5 hours. The reaction product is then withdrawn from the bottom and sent into a second reactor (IIb), referred to as a saponification finisher, which is kept at 80° C. by the external circulation of hot water and receives 30% strength sodium hydroxide solution at a flow rate (1,000 g/hour) which is such that the pH of the reaction medium is kept at 8-8.5.

The mixture of sodium ethyl-phosphite, ethanol, water and sodium chloride is withdrawn from the reactor IIb and then treated as in Example 1.

EXAMPLE 3

The procedure of Example 1 is followed, except that the sodium hydroxide is replaced by potassium hydroxide. The conditions and the yields of isolated product are very similar to those of the preceding example.

EXAMPLE 4

The procedure of Example 1 is followed, except that the sodium hydroxide is replaced by ammonia, and that the latter is used in a 5% excess, relative to stoichiometry. A concentrated solution of ammonium ethyl-phosphite is obtained because of the greater solubility of ammonium ethyl-phosphite in water (65%).

A solution containing ammonium ethyl-phosphite (44%) and ammonium chloride (18.5%) is reacted, at 90° C. for 1 hour (residence time), with a solution containing aluminium sulphate (40%). The results are similar, whether one reactor (temperature $\leq$ 80° C. and pH $\leq$ 8.5) or two reactors II are used.

The yield of aluminium ethyl-phosphite is 89% relative to the ammonium ethyl-phosphite and about 86% relative to the phosphorus trichloride employed.

EXAMPLE 5

The procedure of Example 1 is followed, except that the aluminium sulphate is charged into the reactor III as crystals of $Al_2(SO_4)_3.15H_2O$ at a rate of 433 g/hour. The temperature for the double decomposition is 80° C. and the residence time is 1 hour 30 minutes, i.e. longer than that in the case of the solution because it is necessary to ensure the dissolution of the solid sulphate. After filtration, washing and drying under the same conditions as in Example 1, dry aluminium ethyl-phosphite (425 g/hour) is obtained with a yield of 93.5% relative to the sodium ethyl-phosphite and 90% relative to the phosphorus trichloride employed.

EXAMPLE 6

The procedure of Example 1 is followed, the aluminium sulphate being replaced, in the double decomposition stage, by hydrated aluminium nitrate containing $9H_2O$, which is more soluble in water (55% at 80° C.).

Furthermore, since it is more soluble than sodium sulphate, the sodium nitrate resulting from the reaction assists the formation of the aluminium ethyl-phosphite by increasing the salt effect.

Under these conditions, the aluminium ethyl-phosphite is obtained with a yield of 91% relative to the sodium ethyl-phosphite and 87% relative to the phosphorus trichloride.

EXAMPLE 7

The procedure of the preceding example is followed, except that the alcohol is not removed in the second stage. The double decomposition is therefore carried out starting from an aqueous-ethanolic solution containing sodium ethyl-phosphite (25.5%), sodium chloride (9.5%) and aluminium nitrate (800 g/hour).

After filtration, aluminium ethyl-phosphite is obtained which has a very similar particle size distribution to that indicated in Example 1 and a slightly greater moisture content, i.e. 9%.

EXAMPLE 8

The procedure of Example 1 is followed, the aluminium sulphate being replaced by sodium aluminate, $Al_2O_3.2Na_2O$, to which has been added a sufficient amount of hydrochloric acid to achieve the required pH.

Under these conditions, the aluminium ethyl-phosphite is obtained with a yield of 60%.

EXAMPLE 9

The procedure of Example 1 is followed, except that stage A is carried out as follows:

A mixture of diethyl phosphite (90 mol %) and phosphorous acid (10%) is heated at 150° C. for 30 minutes.

This yields a mixture containing diethyl phosphite (76.5%), monoethyl phosphite (22%) and phosphorous acid (1.4%). This mixture is cooled and then led towards the reactor II in which it is treated as in Example 1, except that the flow rate of sodium hydroxide is lower, because there is no longer any dissolved hydrochloric acid to be neutralised.

EXAMPLE 10

The procedure of Example 1 is followed, except that, in the double decomposition stage C, sodium sulphate (120 g/hour) is added to the reaction medium.

Under these conditions, the yield of aluminium ethyl-phosphite is 90% (instead of 88% in Example 1), relative to the sodium ethyl-phosphite.

We claim:

1. A process for the continuous manufacture of aluminium monoethyl-phosphite, which consists in successively:
   (a) preparing a mixture of phosphite compounds, containing at least 70 mol % of diethyl phosphite,
   (b) saponifying and neutralising this mixture with an inorganic base at a temperature of 20° to 85° C., whilst keeping the pH at 4.0 to 8.5, and then
   (c) reacting the residual aqueous solution of alkali metal monoethyl-phosphite, which is continuously withdrawn from the preceding operation, with an approximately stoichiometric amount of a water-soluble aluminium salt, at a temperature of 70° to 95° C. and at a pH of about 3.0 to 4.5, and continuously withdrawing the precipitate of aluminium monoethyl-phosphite.

2. A process according to claim 1, which comprises starting from a mixture of phosphite compounds containing at least 70 mol % of diethyl phosphite, from 1 to 25 mol% of monoethyl phosphite and from 0 to 2 mol % of phosphorous acid.

3. A process according to claim 2, in which the mixture of phosphite compounds is obtained by reaction of phosphorus trichloride and ethanol at a temperature between 30° and 80° C.

4. A process according to claim 3, in which the ethanol employed contains at most 15% by weight of water.

5. A process according to claim 3, in which the mixture of phosphite compounds is then freed of the hydrochloric acid produced by the reaction for obtaining this mixture.

6. A process according to claim 2, in which the mixture of phosphite compounds is obtained by the reaction, at a temperature of about 150° C., of a binary mixture containing at least 85 mol % of diethyl phosphite and at most 15 mol % of phosphorous acid.

7. A process according to one of claims 1 to 6, which comprises using sodium hydroxide, potassium hydroxide or ammonia as the inorganic base.

8. A process according to claim 1, in which the saponification and neutralisation reaction is carried out continuously in a reactor, at a pH between about 7 and 8 and at a temperature of 65° to 85° C.

9. A process according to claim 1, in which the saponification and neutralisation reaction is carried out continuously in two stages, the first being at a temperature of 30° to 60° C. and at a pH equal to at most 4.5, and in which the reaction is completed at a pH equal to at most 8.5 and at a temperature of 60° to 85° C.

10. A process according to claim 1, in which the ethanol produced by the saponification and the neutralisation is removed continuously by distillation in the form of an aqueous-alcoholic mixture.

11. A process according to claim 10, in which the aqueous-alcoholic mixture separated off by distillation is recycled continuously into the first stage of the process.

12. A process according to claim 1, in which the double decomposition is carried out starting from an excess of up to 20 mol % of water-soluble aluminium salt.

13. A process according to claim 12, which comprises employing an excess, ranging up to 10 mol %, of water-soluble aluminium salt.

14. A process according to claim 1, which comprises employing aluminium sulphate.

15. A process according to claim 14, in which the aluminium sulphate is added as a solid.

16. A process according to claim 14, in which the aluminium sulphate is added as an aqueous solution.

17. A process according to claim 13, which comprises employing aluminium nitrate.

18. A process according to claim 13, which comprises using an alkali metal aluminate and adding a strong acid to a pH of about 4.

19. A process according to claim 1, which comprises adding a water-soluble inorganic salt to the reaction medium in the double decomposition stage.

20. A process according to claim 19, in which the water-soluble inorganic salt is sodium sulphate.

21. A process of making aluminium monoethylphosphite comprising
(a) providing a mixture of at least 70 mol % diethyl phosphite, 1-25% monoethyl phosphite and 0-2% phosphorous acid;
(b) continuously saponifying the diethyl phosphite and neutralizing the monoethyl phosphite and acid with a 20-50% aqueous solution of strong inorganic base for about 1-6 hours at 30°-85° C. and a pH of 4.0-8.5, and continuously distilling of ethanol formed during said saponifying and neutralizing stage and thereby providing an aqueous solution of about 20-70% Me monoethyl phosphite;
(c) continuously subjecting said aqueous solution of Me monoethyl phosphite to double decomposition by reaction with up to 20 mol % excess of water-soluble aluminum salt at 70°-95° C. and pH 3.0-4.5 for at least 30 minutes to form aluminum monoethyl phosphite precipitate; and
(d) recovering and washing the precipitate.

UNITED STATES PATENT AND TRADEMARK OFFICE
CERTIFICATE OF CORRECTION

PATENT NO. : 4,272,448
DATED : June 9, 1981
INVENTOR(S) : BERNARD et al

It is certified that error appears in the above-identified patent and that said Letters Patent are hereby corrected as shown below:

Column 5, line 31, "empolyed" should read --employed--
          line 33, "move" should read --more--
Column 6, line 1 of Example 1, "55 g/hour" should read --550 g/hour--
          line 18, "75°" should read --75°C--

Signed and Sealed this

Thirteenth Day of July 1982

[SEAL]

Attest:

GERALD J. MOSSINGHOFF

Attesting Officer

Commissioner of Patents and Trademarks